United States Patent
Hang et al.

(10) Patent No.: US 12,383,467 B2
(45) Date of Patent: Aug. 12, 2025

(54) SYRINGE ASSEMBLY

(71) Applicant: Becton, Dickinson and Company, Franklin Lakes, NJ (US)

(72) Inventors: Tianqi Hang, Newark, NJ (US); David Poganski, Airmont, NJ (US); Amit Uday Limaye, Wayne, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1168 days.

(21) Appl. No.: 17/257,835

(22) PCT Filed: Jan. 31, 2019

(86) PCT No.: PCT/US2019/016046
§ 371 (c)(1),
(2) Date: Jan. 4, 2021

(87) PCT Pub. No.: WO2020/013886
PCT Pub. Date: Jan. 16, 2020

(65) Prior Publication Data
US 2021/0315776 A1    Oct. 14, 2021

Related U.S. Application Data

(60) Provisional application No. 62/696,036, filed on Jul. 10, 2018.

(51) Int. Cl.
*A61M 5/31* (2006.01)
*A61J 1/20* (2006.01)
(Continued)

(52) U.S. Cl.
CPC .......... *A61J 1/2096* (2013.01); *A61J 1/2065* (2015.05); *A61M 5/178* (2013.01);
(Continued)

(58) Field of Classification Search
CPC ........ A61J 1/2051; A61J 1/2065; A61J 1/201; A61J 1/1406; A61J 1/2096; A61M 5/178; A61M 5/46; A61M 5/34; A61M 5/1782; A61M 5/3257; A61M 5/3134; A61M 2005/3114
See application file for complete search history.

(56) References Cited

U.S. PATENT DOCUMENTS

| | | |
|---|---|---|
| 5,002,533 A | 3/1991 | Jullien |
| 7,497,841 B2 | 3/2009 | Alchas |

(Continued)

FOREIGN PATENT DOCUMENTS

| | | |
|---|---|---|
| EP | 1930038 A2 | 6/2008 |
| EP | 2853278 A2 | 4/2015 |

(Continued)

OTHER PUBLICATIONS

International Search Report dated May 6, 2019, which issued in the corresponding PCT Patent Application PCT/US2019/016046.

*Primary Examiner* — Tasnim Mehjabin Ahmed
(74) *Attorney, Agent, or Firm* — Dickinson Wright PLLC

(57) ABSTRACT

A syringe assembly (10, 80, 132, 192) includes a syringe barrel (12, 86, 134, 194) having a proximal end and a distal end, a needle (18, 89, 140, 200) coupled to the distal end of the syringe barrel, a body (22, 142, 202) coupled to the syringe barrel, and movable shield (24, 82, 164, 222) for moving in an axial direction between a first position where the needle is exposed and a second position covering at least a portion of the needle. The body (22, 142, 202) is configured for enabling the shield (24, 82, 164, 222) to move to the second position and retain the shield in the second position. The shield (24, 82, 164, 222) can slide axially, and rotate relative to the body or slide transversely relative to the body when the shield is in the second position.

19 Claims, 18 Drawing Sheets

(51) Int. Cl.
  *A61M 5/178* (2006.01)
  *A61M 5/32* (2006.01)
  *A61J 1/14* (2023.01)
  *A61M 5/34* (2006.01)
  *A61M 5/46* (2006.01)

(52) U.S. Cl.
  CPC ........ *A61M 5/1782* (2013.01); *A61M 5/3134* (2013.01); *A61M 5/3257* (2013.01); *A61J 1/1406* (2013.01); *A61J 1/201* (2015.05); *A61M 2005/3114* (2013.01); *A61M 5/34* (2013.01); *A61M 5/46* (2013.01)

(56) References Cited

U.S. PATENT DOCUMENTS

| | | |
|---|---|---|
| 8,801,673 B2 | 8/2014 | Zaiken et al. |
| 2003/0105430 A1 | 6/2003 | Lavi et al. |
| 2004/0111064 A1* | 6/2004 | Asbaghi ............. A61M 5/3272 604/198 |
| 2005/0054987 A1 | 3/2005 | Perez et al. |
| 2009/0299295 A1 | 12/2009 | Rubinstein et al. |
| 2011/0160675 A1 | 6/2011 | Ruan et al. |
| 2014/0088512 A1 | 3/2014 | Quinn |
| 2017/0056600 A1 | 3/2017 | Schoonmaker |

FOREIGN PATENT DOCUMENTS

| | | |
|---|---|---|
| EP | 3181167 A2 | 6/2017 |
| JP | H03-158171 A | 7/1991 |
| JP | 2011-524767 A | 9/2011 |
| JP | 2013-526364 A | 6/2013 |
| JP | 3194715 U | 11/2014 |
| JP | 2016-520364 A | 7/2016 |
| JP | 2017056230 A | 3/2017 |
| WO | 2009114762 A1 | 9/2009 |
| WO | 2010053570 A1 | 5/2010 |
| WO | 2011146042 A1 | 11/2011 |

* cited by examiner

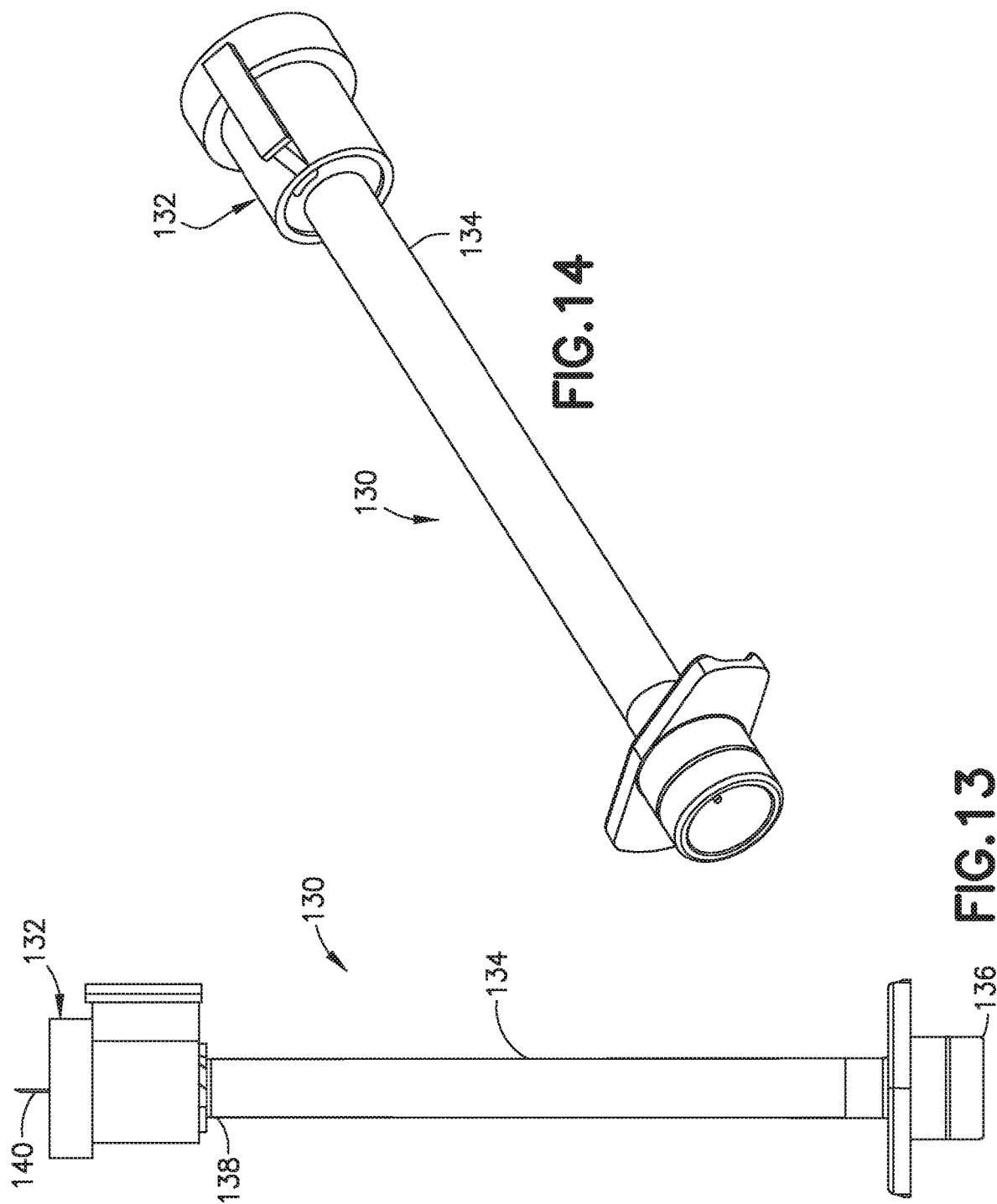

SYRINGE ASSEMBLY

This application claims priority to U.S. Provisional Patent Application No. 62/696,036, filed on Jul. 10, 2018, which is hereby incorporated by reference in its entirety.

FIELD OF THE INVENTION

The invention is directed to syringe assembly having a movable member for modifying the length of the exposed portion of the syringe needle. The syringe has a movable shield that moves relative to the syringe body to reduce the length of the exposed end of the needle to limit a depth of penetration of the needle into the patient.

DESCRIPTION OF THE RELATED ART

Needle lengths in the range of 4 mm to 5 mm can be difficult to insert into a container or vial and aspirate due to the short length. The short length requires the needle to pierce septum in the vial in a straight line to ensure penetration and reduce the risk of the needle bending.

The insertion of a needle into the skin of a patient is determined primarily on the features of the needle and not the features or structure of the needle support as disclosed in Needle Insertion Modeling; Indentifiability and Limitations, L. Barbe, Biomedical Signal Processing and Control 2 (207) 191-198. Needle insertion into the skin of patient is generally classified into three phases that influence the injection depth. The first phase corresponds to the initial contact of the needle with the skin where the tissue deforms without puncturing the surface of the skin. A second phase refers to the puncture of the skin and the relaxation of the skin when the insertion force of the needle is stopped. The third phase is where the needle is extracted and pulls or stretches the skin outward as the needle is extracted.

Needle lengths, such as needles having a length of about 4 mm to 5 mm are adapted to inject a medication to a specified target depth in a subcutaneous region. The present invention provides a structure so that a needle can be consistently inserted to a desired target depth. Prior pen needles have the cannula supported on an axial post extending from the hub. The post forms a narrow portion and a relatively wider base that does not contact the skin during the injection. In other pen needles known in the art, a distal face of the hub placed against the injection site may be relatively large, and may be provided with a slight taper at the edge. The edge of the hub can engage the skin when the cannula is inserted at an angle relative to the surface of the skin of the patient.

Various injection devices have been produced where the supporting structure does not contact the skin during injection or extraction of the needle. Other devices have been proposed where the end face of the device is positioned to contact the surface of the skin to limit the depth of penetration into the patient.

Pen-injector delivery devices facilitate self-administration of parenteral medications. Pen needles are a component of needle-based injection systems and consist of a doubled ended cannula assembled into a plastic hub using adhesive. The hub has internal threads, which allow it to be attached to the pen-injector device. Pen needle attachment allows the proximal end of cannula to penetrate through the rubber septum of the medicament cartridge to create the fluid flow path. For many diabetics maintaining blood glucose control is achieved by performing multiple daily injections of insulin into the subcutaneous (SC) tissue using pen injector delivery devices developed to be a convenient, discreet alternative to the vial and syringe. Numerous pen injectors are commercially available in either disposable or multi-use configurations, each offering various patient-centric features. The distal pen needle cannula interfaces with the delivery site providing a conduit for delivery. Pen needle designs are intended to enable consistent delivery to the target tissue space, minimize leakage of injectate, and reduce pain/discomfort and site effects such as bleeding and bruising associated with the injection. The primary design features, needle length/gauge and hub face geometry, in conjunction with mechanics of the delivery system and injection technique, dictate injection success.

Injections may be performed in the intradermal region, the subcutaneous region and the intramuscular (IM) region of the skin. For many types of injectable medications, including insulin, the SC region is preferred for administering an injection, See, for example, Lo Presti, et al., Skin and subcutaneous thickness at injecting sites in children with diabetes: ultrasound findings and recommendations for giving injection, *Pediatric Diabetes* (2012).

An example of a prior device is disclosed in U.S. Pat. No. 9,937,299 where the device is a syringe with an assembly for adjusting the depth of penetration of the needle. The assembly includes a collar attached to the syringe that is movable with respect to the syringe.

While the prior devices are generally suitable for the intended use, there is a continuing need for improved devices for controlling the depth of penetration of a cannula for delivering a drug or medicament to a selected target area.

SUMMARY OF THE INVENTION

The present invention is directed to syringe assembly to assist in filling and/or aspirating the syringe and modifying the exposed length of the distal end of the needle to limit a depth in the skin of the patient. The invention in one embodiment has a syringe assembly that provides the needle with a first exposed length for filling and aspirating the syringe and a second exposed length for injecting the substance to the desired depth into the skin. In the embodiments described, the second exposed length of the needle is less than the first exposed length. The syringe assembly has a movable shield to cover a portion of the needle to reduce the effective length of the exposed portion of the needle to control a depth of penetration of the needle into the patient.

The syringe assembly in one embodiment includes a syringe barrel and a needle extending from a distal end of the syringe barrel. A movable shield member is coupled to the syringe barrel for sliding movement relative to the needle and the syringe body. The movable shield member slides between a first retracted position where the needle is exposed a first length for filling the syringe with a substance from a container or reservoir, and a second position extending at least partially over the proximal end of the needle to reduce the length of the exposed portion of the needle. In one embodiment, the movable shield member has a collar at a distal end that Moves over the proximal end of the needle in an axial direction to reduce the length of the exposed portion of the needle extending from the syringe and to limit a depth of penetration of the needle into the patient.

In one embodiment, the syringe assembly includes a syringe barrel with a body attached to a distal end. A movable shield member is mounted on the body for sliding between a retracted position to expose the needle on the syringe, and an extended position covering a portion of the proximal end of the needle. The movable shield member includes a retaining mechanism for retaining the movable shield member in the extended position during use of the syringe. The movable shield member slides over the end of the syringe in an axial direction with respect to the longitudinal axis of the syringe.

In one embodiment, the syringe barrel has a movable shield member that slides between a retracted position to expose the needle, and an extended position covering a portion of the needle. The shield member has at least one retaining mechanism that cooperates with a retaining mechanism on the syringe to retain the shield member in the extended position.

In one embodiment, the movable shield member slides to an extended position where the retaining mechanism engages the retaining mechanism on the syringe to retain the movable shield member in the extended position. In other embodiments, the movable shield member rotates in the extended position to engage the retaining mechanism. In another embodiment, the movable shield member is configured to slide in a transverse direction relative to the longitudinal axis of the syringe when the shield member is in the extended position to engage the retaining mechanism and retain the shield member in the extended position. The shield member can also have a slot engaging a detent on the syringe where the slot has a first portion to enable sliding movement in an axial direction and rotational movement when the shield member is in the extended position.

The features are basically attained by providing a syringe assembly comprising a syringe barrel having a proximal end and distal end, a needle hub at the distal end of the syringe barrel, and a movable shield member that is movable relative to the syringe barrel between a first position where the needle is exposed and a second position covering a portion of the needle. The shield member is configured for engaging a retaining mechanism on the syringe barrel to retain the shield member in the extended position.

The features of the syringe assembly are also provided by a syringe barrel having a proximal end and a distal end, and a needle extending from the distal end of the syringe barrel. An adapter can be coupled to the distal end of the syringe barrel for supporting a movable shield member where the shield member moves between a first position to expose a first portion of the needle having a first length, and a second position to expose a second portion of the needle having a second length less that the first length.

A method is provided for filling a syringe with a medication or other substance, The method comprises providing a syringe barrel having a proximal end and a distal end, a needle extending from the distal end of said syringe barrel, and a movable shield member on the distal end of the syringe barrel. The shield member is movable between a first position to expose a first portion of the needle having a first length, and a second position to expose a second portion of the needle having a second length less than the first length. The method moves the shield member to the first position to expose the needle for piercing a septum of a container or vial and retracting the syringe plunger to suction a substance into the syringe. The shield member moves to the second position to expose the second portion of the needle for penetrating the skin of the patient for use in injecting the substance to a controlled depth in the patient.

These and other features of the invention will become apparent from the following detailed description of the invention, which in conjunction with the drawings disclose various embodiments of the invention.

BRIEF DESCRIPTION OF THE DRAWINGS

The following is a brief description of the drawings in which:

FIG. 13 is a side view of the syringe assembly in a further embodiment showing the shield member in a retracted position;

FIG. 14 is a perspective view of the syringe assembly of FIG. 13;

DETAILED DESCRIPTION OF THE INVENTION

Figure 1:
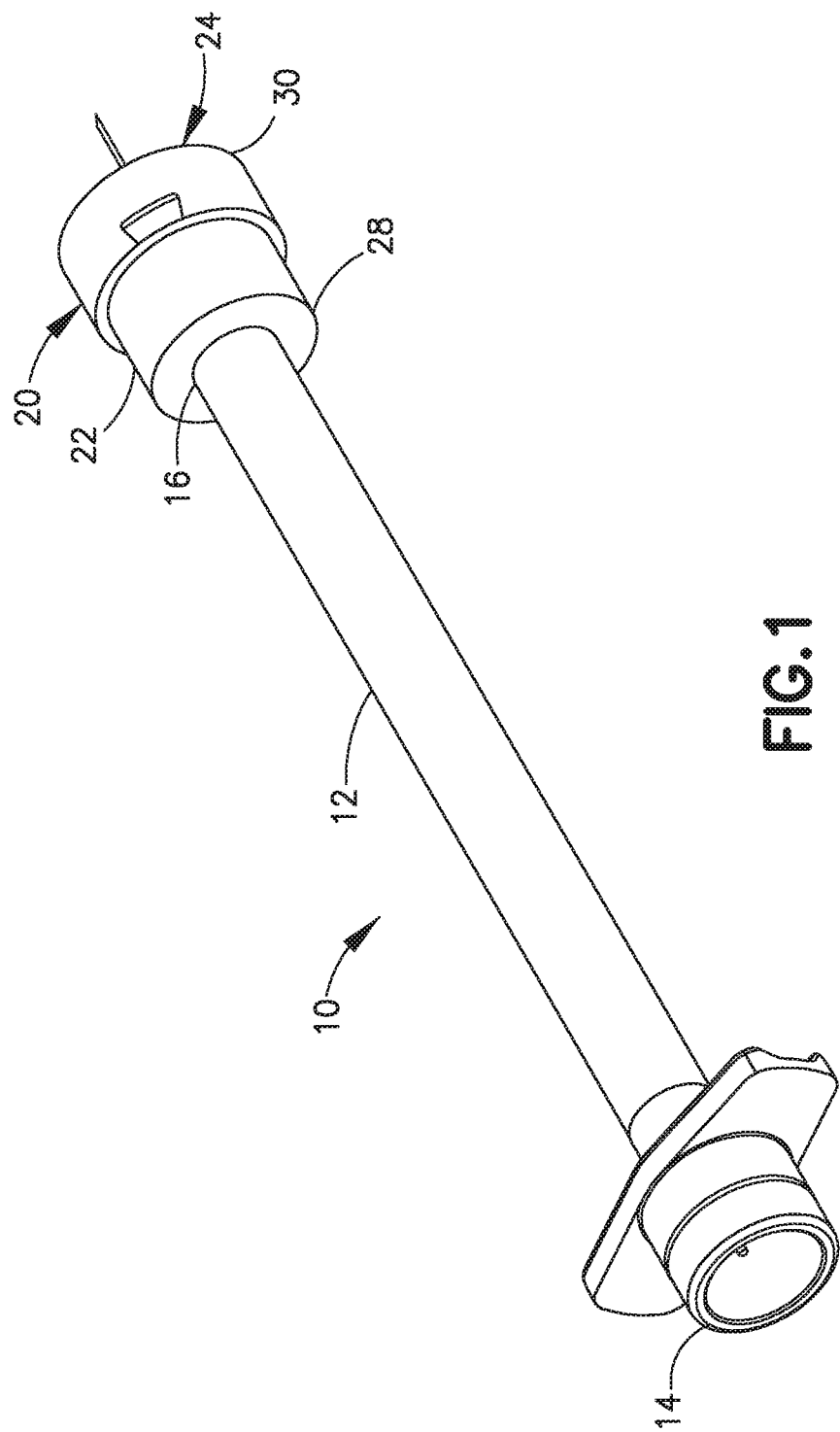
FIG. 1 is a perspective view of the syringe assembly in one embodiment of the invention.
Figure 2:
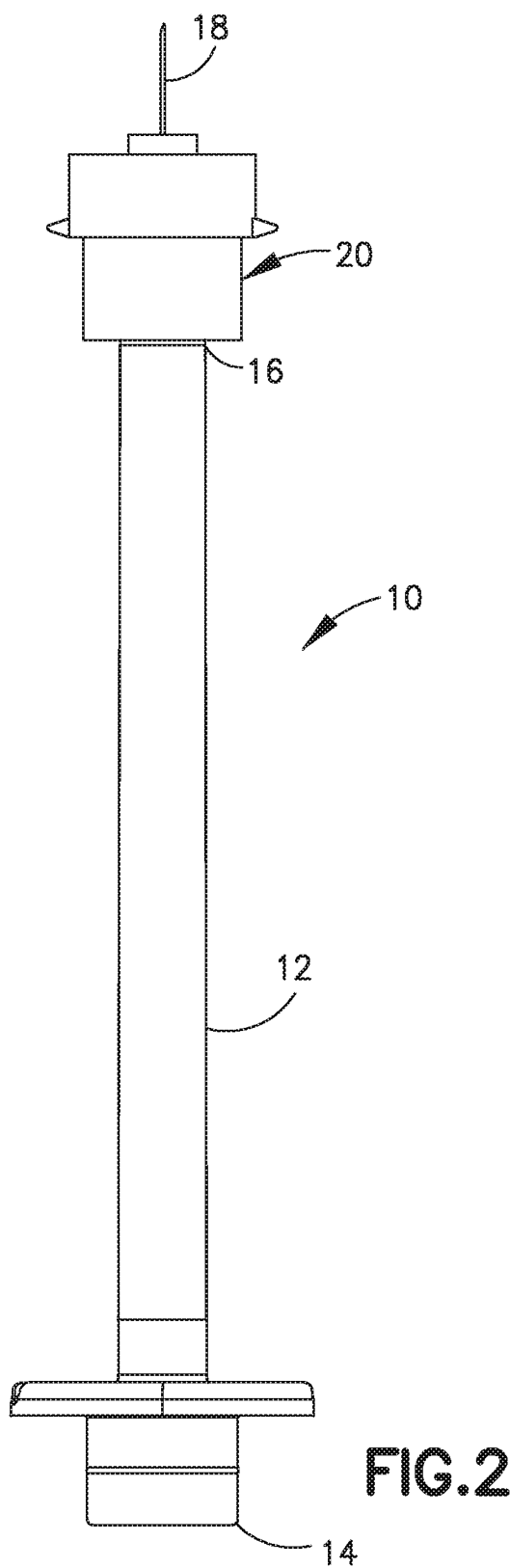
FIG. 2 is a side view of the syringe assembly of FIG. 1.

The syringe assembly of the invention refers to a syringe having a needle or cannula for injecting a medication or other substance into a patient. The terms needle and cannula are used herein interchangeably to refer to a thin tubular member having a sharp end for insertion into an injection site on a subject. A distal direction is in the direction toward the injection site, and the proximal direction is the opposite direction. The axial direction refers to a direction along or parallel to the longitudinal axis of the needle and the needle hub and the radial direction refers to a direction perpendicular to the axial direction.

The intradermal layer in adults generally has a thickness of around 2 to 3 mm, so that intradermal injection depth is in a range of about 3 mm or less as measured from the outer surface of the skin. The thickness of the subcutaneous layer varies depending on the age of the patient, gender, body mass index (BMI), and the part of the body where the injection is administered. The subcutaneous region has an average thickness of about 7 mm to about 15 mm. Insulin is preferably delivered to the subcutaneous region. The syringe assembly is configured for controlling the depth of penetration of the needle to a selected depth, such as for example a depth of 3 mm or less.

The syringe assembly is suitable for use in a method for injections and for injecting a drug to a patient. The above description of the preferred embodiments is not to be deemed as limiting the invention, which is defined by the appended claims. The disclosure is intended to enable the artisan of ordinary skill to practice variants of the invention described without departing from the scope of the invention. Numerical limitations herein, in the specification and in the claims, are understood to be limited by the modifier "about," such that minor departures yielding equivalent results is within the scope of the invention. Features or dependent claim limitations disclosed in connection with one embodiment or independent claim may be combined in another embodiment or with a different independent claim without departing from the scope of the invention.

The syringe assembly is configured for introducing a substance, such as a drug, to a selected depth in the patient while providing a needle length sufficient for ease of filling or aspirating the substance into the syringe. Referring to FIGS. 1-7, the syringe assembly 10 includes a syringe barrel 12 and a needle shield assembly 20. The syringe barrel has a proximal end 14 and a distal end 16. The proximal end 14 has an open end that receives a movable plunger having a stopper for dispensing the substance contained in the syringe assembly. For ease of illustration, the plunger is not shown in the drawings although it is understood that the plunger has a known configuration for sliding axially in the syringe barrel to fill the syringe and to dispense the contents of the syringe.

A needle hub is at the distal end 16 of the syringe barrel 12 for supporting a needle 18 in a known manner. The needle 18 extends axially from the needle hub a distance for penetrating the skin of the patient and delivering the substance to the patient. The needle hub can be integrally formed with the distal end of the syringe or configured as a separate member for coupling to the distal end of the syringe barrel 12. The needle shield assembly 20 fits over the needle hub so that the needle 18 extends through the needle shield assembly. The needle shield assembly 20 can be attached to the needle hub by a friction fit or interference fit.

Figure 4:
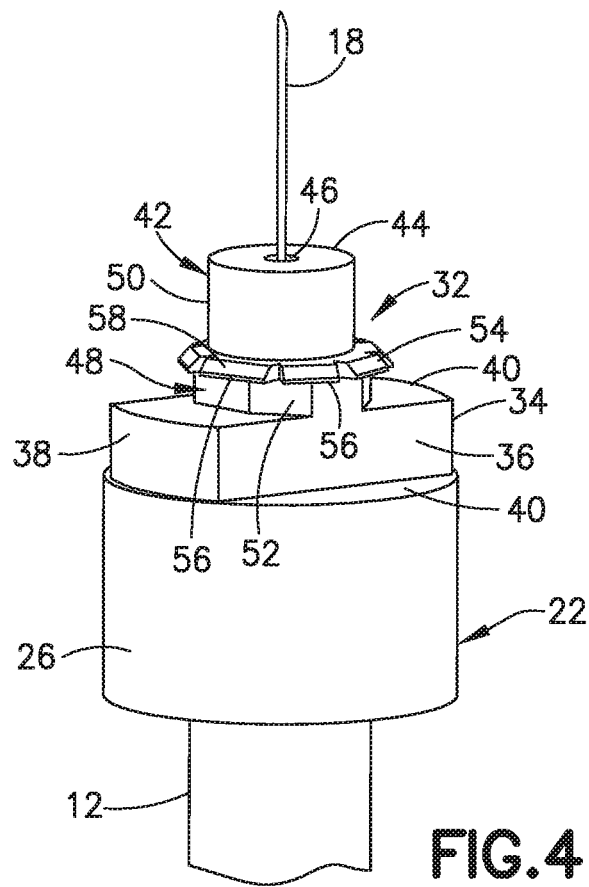
FIG. 4 is a perspective view of the syringe barrel without the movable shield member of the embodiment of FIG. 1.

The needle shield assembly 20 in the embodiment shown has a body 22 and a movable shield member 24 that moves on the body 22 in an axial and rotational direction relative to a longitudinal axis of the syringe and the body 22. The body 22 can be formed with the syringe barrel 12 or can be a separate adapter unit that is coupled to the end of the syringe barrel 12 or the needle hub. In the embodiment shown, the body 22 is a separate adapter member with a center opening to fit onto and couple to the distal end of the syringe and needle hub where the needle 18 extends through the body 22 as shown in FIG. 4. The body 22 has a substantially cylindrical section 26 with a proximal end 28 and a distal end 30.

The body 22 has a retaining mechanism 32 for retaining the shield member 24 on the body 22 and the syringe. The retaining mechanism 32 has a base 34 with a configuration for cooperating with the shield member 20. The base 34 in the embodiment shown extends from the distal end of the body 22 a height sufficient to enable the shield 20 to move between a refracted position and an extended position. The base 34 as shown in FIG. 4 is formed with at least one, and typically two, flat side wall faces 36 extending in the axial direction and curved or rounded end faces 38 extending between the flat faces 36. The curved faces 38 define an outer dimension corresponding substantially to the outer dimension of the body 22. The flat faces 36 converge with a distal face 40 on the distal end of the body 22.

A post 42 extends in the axial direction from the base 22. As shown in FIG. 4, the post 42 has a distal end portion 50 with a substantially cylindrical configuration with a distal end face 44. An opening 46 in the distal end face 44 receives the needle 18 extending from the distal end of the syringe. The post 42 has a first section 48 at a proximal end contiguous with the base 34 and the substantially cylindrical shaped second section 50 for a distal end of the post 42. The first section 48 is formed with a plurality of flat faces 52. In the embodiment shown, the first section 48 has eight faces 50 forming a hexagonal shape. A rib 54 projects radially outward from the post 42 at a distal end of each face 52 of the first section 48. In the embodiment shown, the ribs 54 of each face 52 extend around the circumference of the post 42 and extends radially outward a distance to retain the shield 24 on the post 42. The ribs 42 have a bottom face 56 extending substantially perpendicular to the longitudinal axis of the post 42 and an inclined top face 58 to enable the shield 24 to snap onto the post 42.

Figure 5:
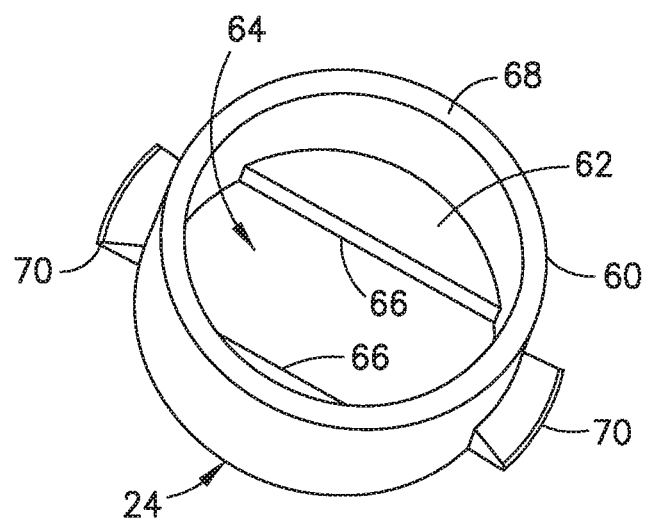
FIG. 5 is a perspective view of the movable shield member.
Figure 7:
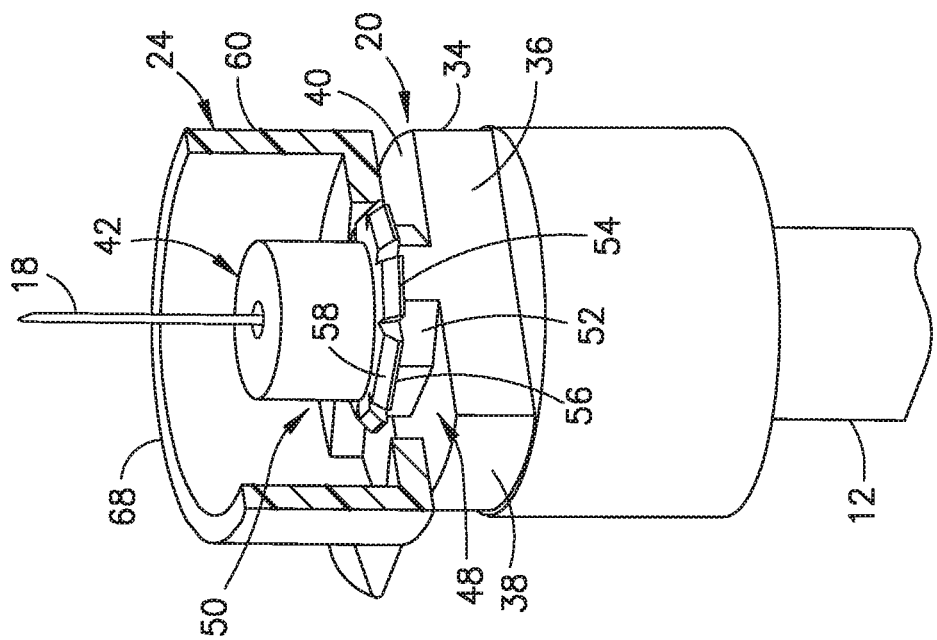
FIG. 7 is a cross-sectional side view of the shield member on the syringe in the extended position.
Figure 6:
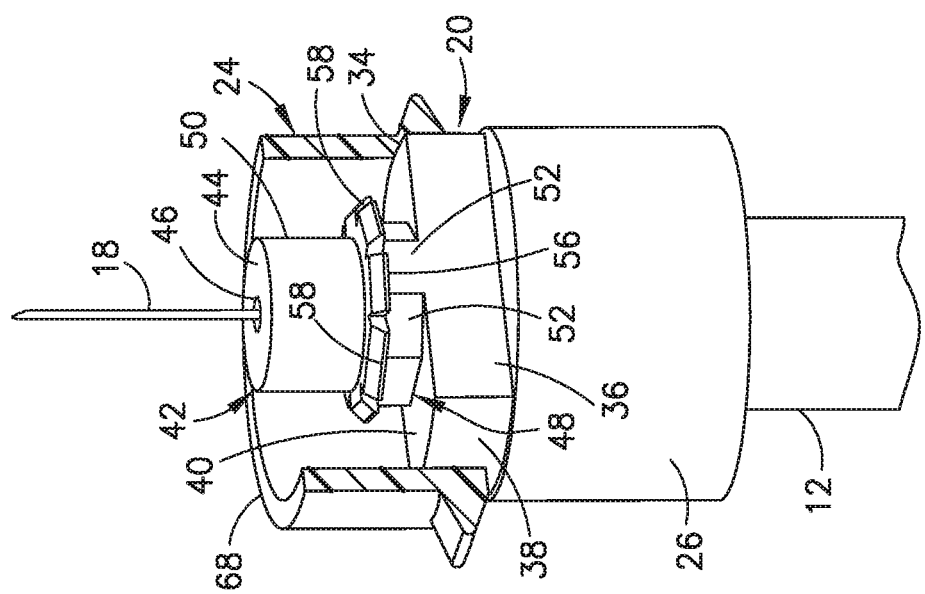
FIG. 6 is a cross sectional view of the shield member on the syringe in the retracted position.
Figure 8:
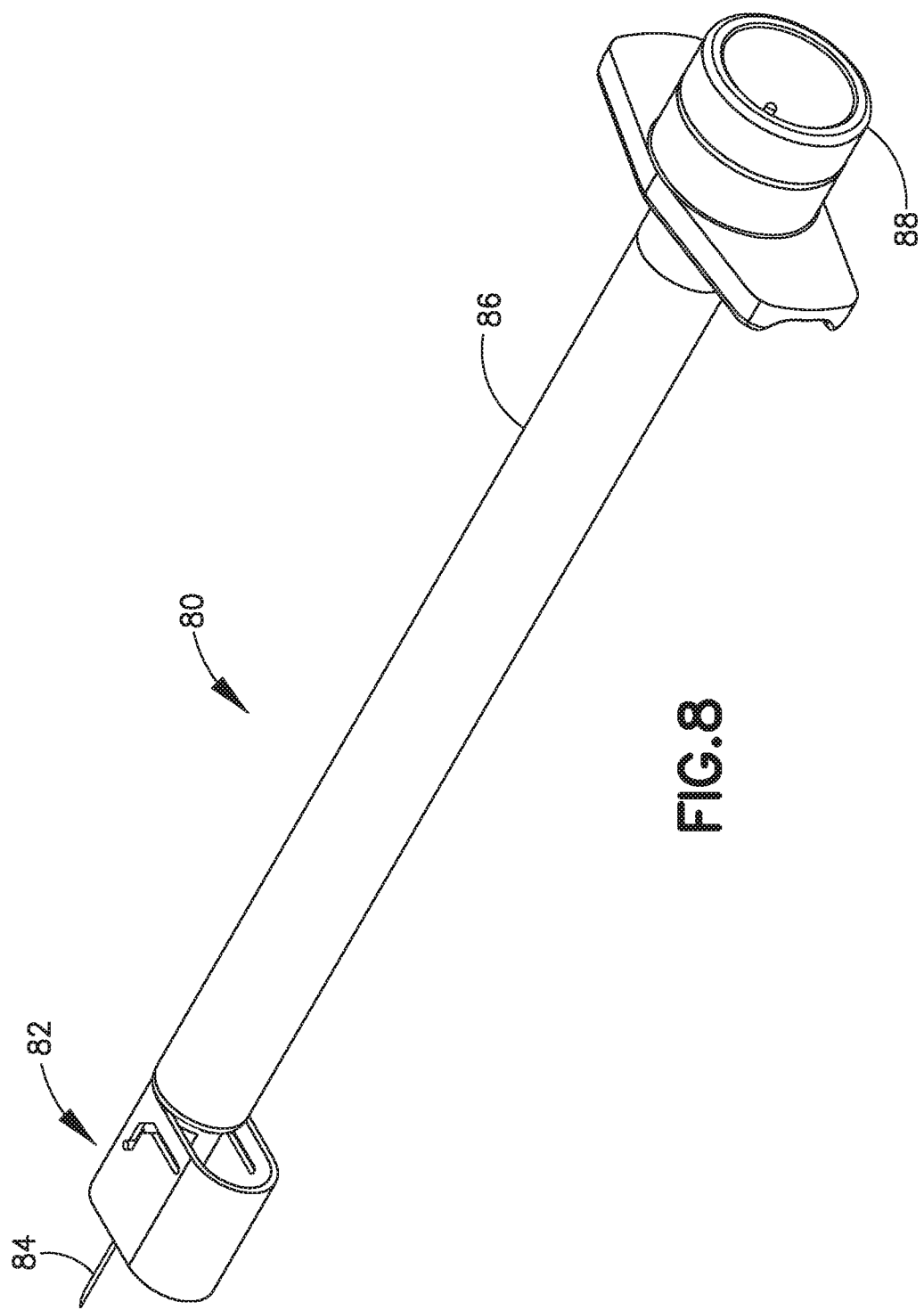
FIG. 8 is a perspective view of the syringe assembly in another embodiment.
Figure 9:
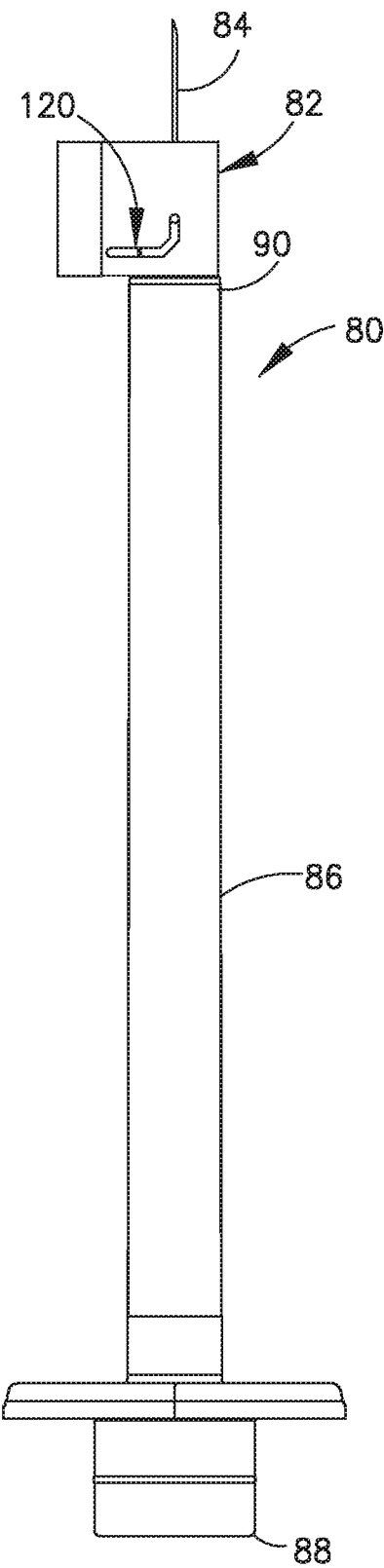
FIG. 9 is a side view of the syringe assembly of FIG. 8.

Referring to FIG. 5, the shield 24 has a substantially cylindrical side wall 60 with a bottom wall 62. The bottom wall 62 has an opening 64 configured for receiving the post 42 and the base 34. The opening 64 in the bottom wall 62 has a shape and configuration for sliding axially on the base 34 where the shield 24 slides between a first retracted position shown in FIGS. 2, 3 and 6 to a second extended position shown in FIG. 7. The opening 64 has inner side edges 66 complementing the flat faces 52 of the post 42 for sliding axially on the post 42. The width of the opening 64 between the inner side edges 66 correspond substantially to the diameter of the first section 48 and less than the diameter of the ribs 54 on opposite sides. The side wall 60 has an axial length to slide from the distal end of the post 42 over a portion of the distal end of the needle 18 as shown in FIG. 7. In the embodiment shown, the side wall 60 has tabs 70 extending outwardly to assist the user in moving the shield 24 on the post 42. The tabs 70 are positioned on opposite sides of the shield in the embodiment shown. The tabs can be located in other suitable positions that enable the user to move the shield in an axial direction and in a rotational direction relative to the syringe.

Figure 3:
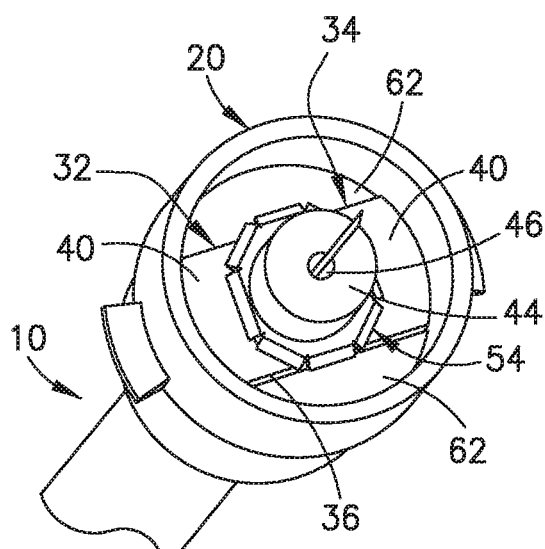
FIG. 3 is a perspective view of the syringe assembly in the embodiment of FIG. 1 showing the movable shield member in a retracted position.

The shield 24 is positioned on the post 42 with the base 34 oriented within the opening 64 in the bottom wall 62. As shown in FIG. 3, the bottom wall 62 is captured by the rib 54 to retain the shield on the base 34. The shield 24 is able to slide axially on the base 34 from the retracted position where the bottom wall 62 contacts the distal surface 40 of the body 22 to the extended position where the bottom wall 62 contacts the bottom face of the ribs 54. The side wall 60 has an axial length where the needle 18 is exposed a first length in the retracted position and the side wall 60 covers a portion of the needle in the extended position. The needle 18 has a length sufficient for inserting through a septum of a drug container to fill and aspirate the syringe when the shield 24 is in the retracted position. In certain instances, the overall length of the needle may be greater than the desired depth of penetration.

The syringe is filled in a standard manner by retracting the plunger to pull the substance from the container for use in injecting the substance to the patient. After the syringe is filled and the needle is separated from the septum of the container, the shield 24 is able to move by sliding axially on the base 34 to the extended position shown in FIG. 6. The side wall 60 of the shield 24 has an axial length where the proximal end of the needle 18 is covered as shown in FIG. 7 such that when the shield is in the extended position, the exposed length of the needle 18 is less than the exposed length of the needle when the shield is in the retracted position. The exposed length of the needle is defined by the length of the needle between the distal end face of the side wall 60 of the shield 24 and the distal tip of the needle 8. The shield 24 moves to the extended position on the base 34 where the bottom wall 62 slides past the end of the base 34, the bottom wall 62 aligns with the first section 48 of the post 42, and the shield is in the extended position. The shield is manually rotated around post 42 where the flat inner edges of 66 of the opening 64 in the bottom wall 62 are captured between the distal end surface 44 of the base 34 and the ribs 54 to retain the shield 24 in the extended position. The straight inner edges 66 of the bottom wall 62 of the shield 24 contact the flat surfaces 52 of the post when the shield is moved to the extended position. The inner edges 66 slide over the flat surfaces 52 so that the corners between the adjacent surfaces 52 form a ratcheting mechanism as the shield rotates and provides a tactile or audible indication that the shield is rotated to the position where the shield is not able to move back to the original retracted position. The flat surfaces 52 retain the angular position of the shield 24 to resist rotation back to the original position where the shield can retract.

As shown in FIG. 7, the shield 24 moves to the extended position to cover a portion of the proximal end of the needle 18 thereby reducing the effective length of the exposed portion of the needle projecting beyond the distal face of the side wall of the shield 24. The needle 18 can pierce the skin to a depth of penetration where the surface of the skin contacts the distal end 68 of the side wall 60 of the shield 24. Rotating the shield 24 to the position shown in FIG. 7 where the bottom wall 62 contacts the surface 40 of the base 34 prevents the shield from retracting when contacting the skin of the patient during the insertion of the needle into the patient. In the embodiment shown, the distal face of the shield slides past the distal face 44 of the post 42 to form a recessed area within the open end of the shield. The distance between the distal face of the post and the distal end of the shield defines a depth of the recess and corresponds to the difference in the exposed length of the needle when the shield in the retracted position and the extended position. The needle 18 has an exposed length as shown in FIG. 7 of about 3-4 mm. The needle 18 has a length extending from the end of the post 42 sufficient to pierce the septum for filling the syringe.

Figure 10:
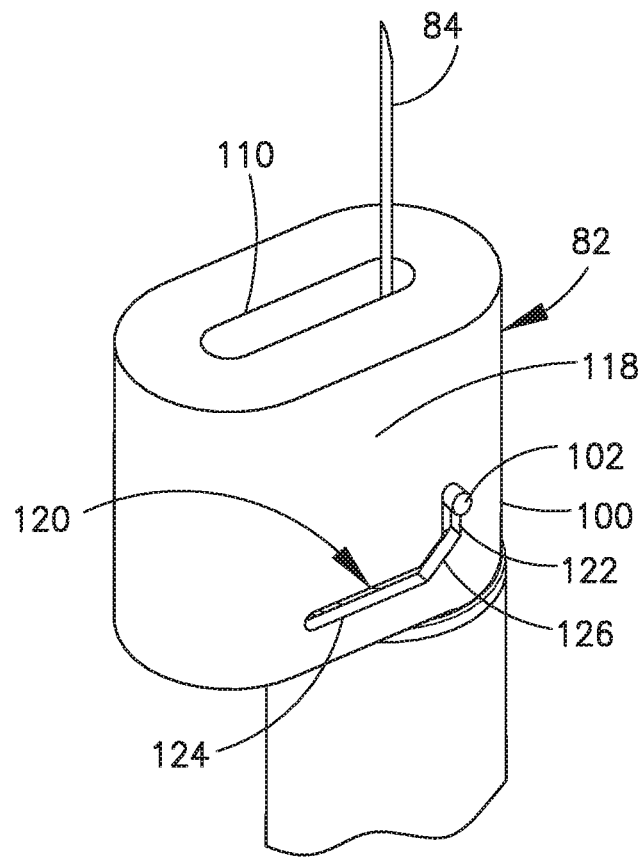
FIG. 10 is a perspective view of the shield member in the embodiment of FIG. 8.
Figure 11:
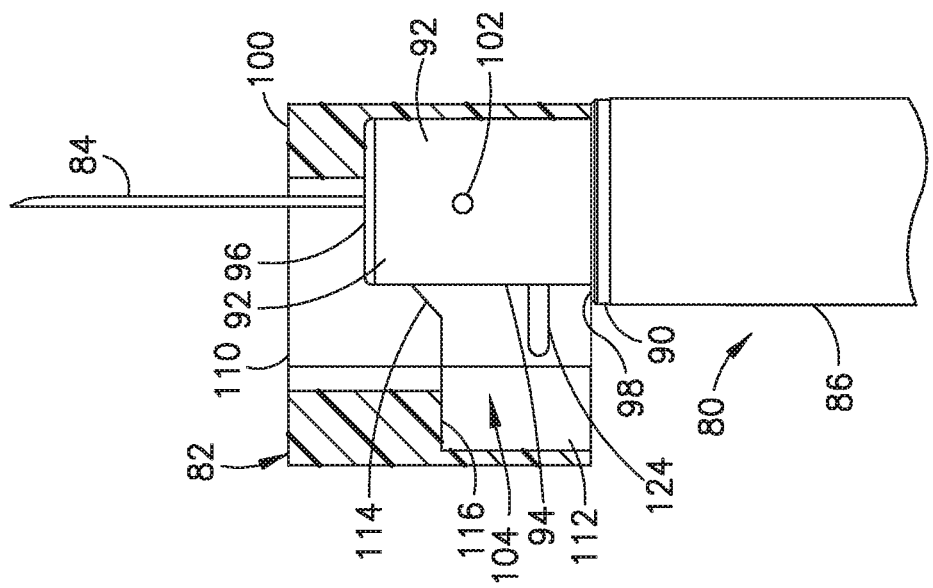
FIG. 11 is a cross sectional view showing the needle shield member in the retracted position.
Figure 16:
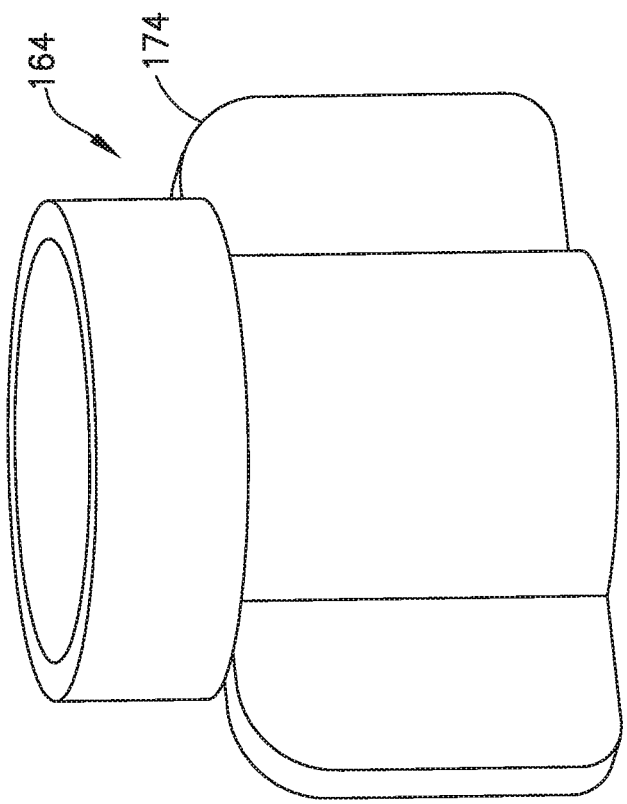
FIG. 16 is a side view of the shield member in an alternative embodiment.
Figure 15:
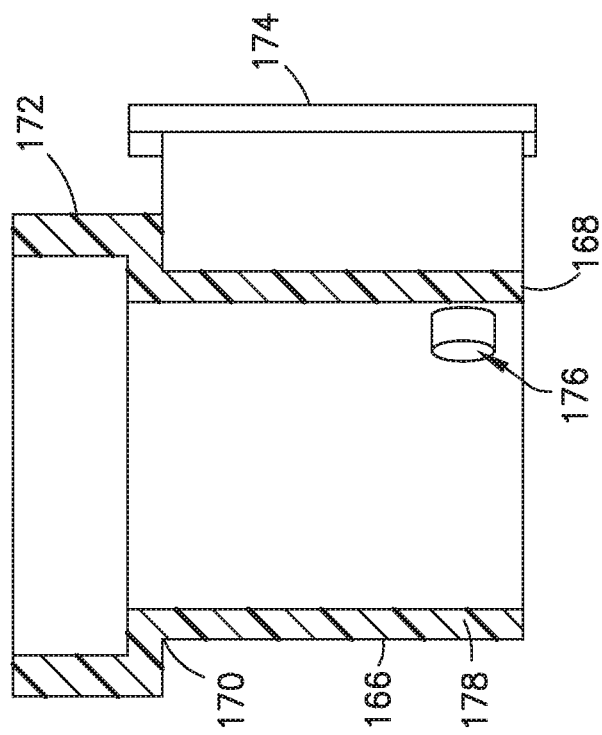
FIG. 15 is a cross sectional view of the shield member in the embodiment of FIG. 13.
Figure 17:
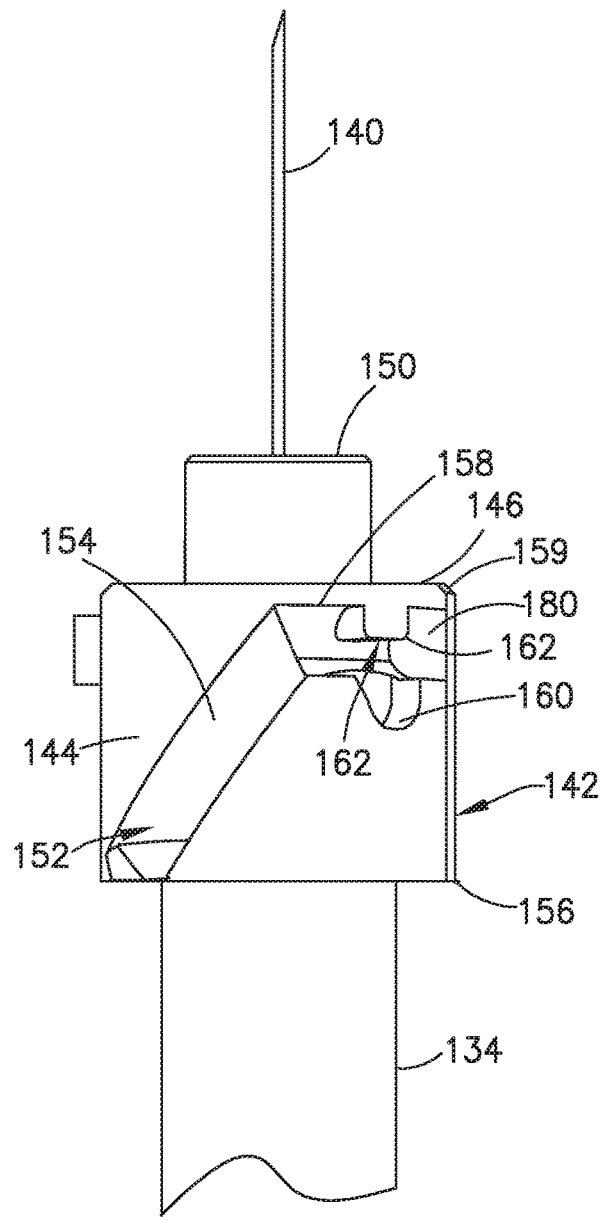
FIG. 17 is a side view of the syringe and adapter showing the guide groove for the shield member of FIG. 13.

Another embodiment is shown in FIGS. 8-12 for the syringe assembly 80 and shield assembly 82 for reducing the effective exposed length of the needle 84. The syringe assembly 80 is similar to the syringe in the previous embodiment and includes a syringe barrel 86 having an open proximal end 88 for receiving a plunger and a distal end 90 supporting the needle 84. The distal end 90 of the syringe barrel in the embodiment shown has a tip 92 having a substantially circular side wall 94 and a distal end surface 96. The side wall of the tip 92 is spaced inwardly from the side wall of the syringe barrel 86 to form an annular shoulder 98 facing in an axial direction. As shown in FIG. 11 in FIG. 12, the needle 84 extends in an axial direction from the tip 92 of the syringe barrel 86. In alternative embodiments, the tip 92 can be a separate member that fits onto the syringe barrel or needle hub where the needle extends through an opening in the tip 92.

The shield assembly 82 includes a shield body 100 cooperating with the decent 102 on the tip 92 of the syringe barrel 86. The shield 100 has a shape and configuration to fit on the tip 92 to slide in an axial direction and to slide in a transverse direction with respect to the longitudinal axis of the syringe 86 and tip 92. The shield 100 has an axial length to expose a first length of the needle 84 when the shield is in a retracted position shown in FIG. 11 and to expose a second length of the needle 84 when the shield is moved to the extended position shown in FIG. 12. As in the previous embodiment, the exposed length of the needle 84 when the shield 100 is in the retracted position is sufficient to enable the needle 84 to pierce the septum of a container for filling the syringe. The exposed length can be about 7-8 mm. The exposed length of the needle when the shield is in the extended position can be about 3-4 mm.

Figure 12:
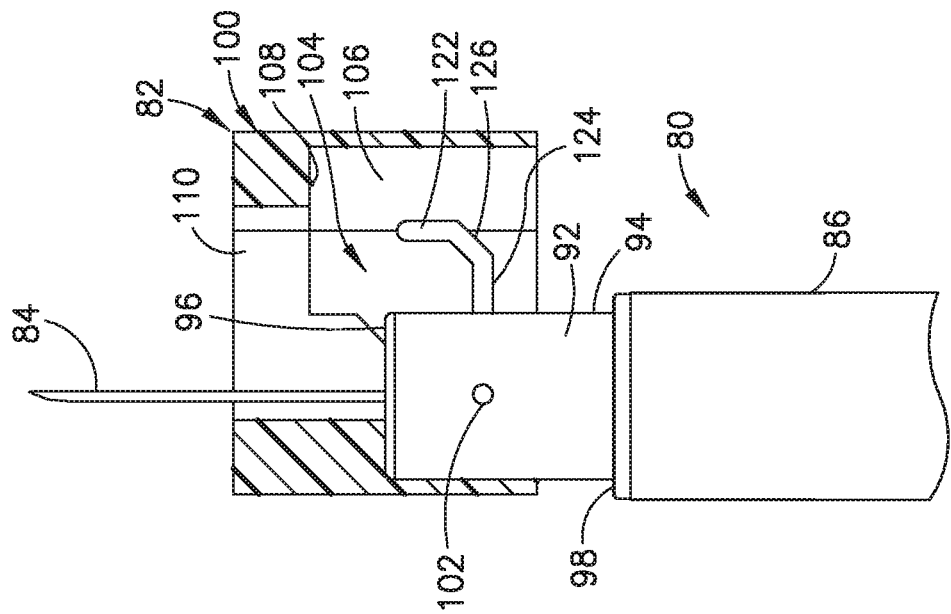
FIG. 12 is a cross sectional view of the syringe assembly showing the needle shield member in the extended position.

Referring to FIGS. 11 and 12, the shield 100 has a cavity 104 at the proximal end of the shield with a dimension for receiving the tip 92 of the syringe assembly 82. The cavity 104 has a first portion 106 shown in FIG. 12 with a dimension for receiving the tip 92 of the syringe assembly. The first portion 106 has an end face 108 and an axial length corresponding substantially to the axial length of the tip 92. The first portion 106 receives the tip 92 when the shield 100 is in the retracted first position shown in FIG. 11 where the shield contacts the shoulder 98 and the distal end 96 contacts the end face 108. The needle 84 extends through the needle opening 110 as shown in FIG. 11 to have a first exposed length sufficient for filling the syringe.

The cavity 104 in the shield 100 has a second portion 112 adjacent the first portion 106 for receiving the tip 92 and having an axial length less than the axial length of the first portion 106. An inclined surface 114 extends between the first portion 106 and the second portion 112. The second portion 112 has an end face 116 shown in FIG. 11 for contacting the distal face 96 of the shield 100 when the shield is in the second extended position shown in FIG. 12. The shield 100 in the position shown in FIG. 12 covers a portion of the proximal end of the needle 84 to reduce the effective length of the exposed portion of the needle extending beyond the distal face of the shield 100. In the position shown in FIG. 12, the needle 84 has an exposed length to deliver the medication to the patient.

The needle opening 110 as shown in FIG. 10 has a width and length to receive the needle 84 and to enable the shield 100 to slide transversely between the position shown in FIG. 11 and FIG. 12. The needle opening 110 is aligned with the cavity 104 and has a dimension less than the dimension of the cavity 104 so that the tip 92 of the syringe barrel 86 does not extend through the needle opening 110.

In the embodiment shown, the shield 100 has an elongated configuration with side walls 118 extending a length corresponding to the longitudinal dimension of the needle opening 110. In the embodiment shown, the side walls 118 are substantially straight and parallel to each other. A guide slot 120 is formed in the respective side walls 118 receiving the detent 102 on the tip 92. The detent 102 captures the needle shield 100 on the tip 92 of the syringe barrel 86 while enabling axial movement and transverse movement of the shield 100 relative to the syringe barrel 86 and tip 92. The guide slot 120 has a first section 122 extending in an axial direction of the shield 100 relative to the syringe barrel 86. The first section 122 has a longitudinal axial length corresponding substantially to the length of travel of the shield in the axial direction between the first portion 106 and second portion 112 of the cavity 104. A second section 124 is connected to the first section 102 by an inclined portion 126. The second section 124 extends in a transverse direction relative to the axial direction of the first section 122 and has a length complementing the longitudinal length of the cavity 104 and the needle opening 110. In the embodiment shown, the detent 102 extends from opposite sides of the tip 92 for connecting to a respective guide slot 120 in the opposite side walls 118. An alternative embodiments, a single detent and guide slot can be provided.

During use of the syringe assembly 80, the shield 100 is initially positioned in the retracted position shown in FIG. 11 where the needle 84 projects from the distal face of the shield 100 to define a first exposed length of the needle. The exposed length of the needle 84 is generally sufficient to pierce the septum of a reservoir or container for filling the syringe in the normal manner. After filling the syringe barrel, the needle is withdrawn from the reservoir where the syringe barrel is ready for use. The shield 100 is moved axially away from the tip 92 by the detent 102 sliding in the first section 122, inclined section 126, and second section 124 of the guide slot 122 to orient the shield 100 in the extended position shown in FIG. 12. The extended position of the shield 100 reduces the effective length of the exposed portion of the needle 84. The shield 100 is manually moved in a transverse direction relative to the longitudinal axis of the syringe barrel where the detent 102 slides in the second section 124 to the position shown in FIG. 12. By positioning the detent 102 in the second transverse section 124, the shield 100 is restricted from sliding axially back to the retracted position.

Referring to FIGS. 13-19, another embodiment of the syringe assembly 130 as shown. The syringe assembly 130 includes a shield assembly 132 for sliding movement relative to the syringe assembly 130. The syringe assembly 130 has a syringe barrel 134 with an open proximal end 136 for receiving a plunger and a distal end 138 supporting a needle 140. In the embodiment shown in FIG. 17, a base 142 in the form of an adapter is connected to the distal end of the syringe barrel 134. The base 142 has a substantially cylindrical shape with a side surface 144 and an axial face 146. A post 148 extends from the base where the post has an end face 150 spaced from the face 146.

The side surface 144 of the base 142 includes a guide groove 152 having a inclined section 154 extending between the proximal end 156 and the distal end 159 of the base 142. The distal end of the guide groove 152 is connected to a transverse section 158 extending in a direction substantially perpendicular to the longitudinal axis of the syringe barrel. The transverse section 158 has a recess 160 and a detent 162 aligned with the recess 160.

The shield assembly 132 includes a shield 164 having a substantially cylindrical shaped body 166 with an inner dimension corresponding to the outer dimension of the base 142 for sliding the shield 164 relative to the base 142. The body 166 has a proximal end 168 and a distal end 170 with an annular collar 172 extending axially from the distal end. The collar 172 in the embodiment shown has a diameter greater than the diameter of the body 166. A tab 174 is provided on the outer surface of the body 166 to assist the user in manipulating the shield 164 relative to the base 142. In the embodiment shown in FIG. 15, a single tab 174 is shown. In an alternative embodiment shown in FIG. 16, more than one tab 174 or flange can be provided to assist the user in manipulating the shield.

Figure 18:
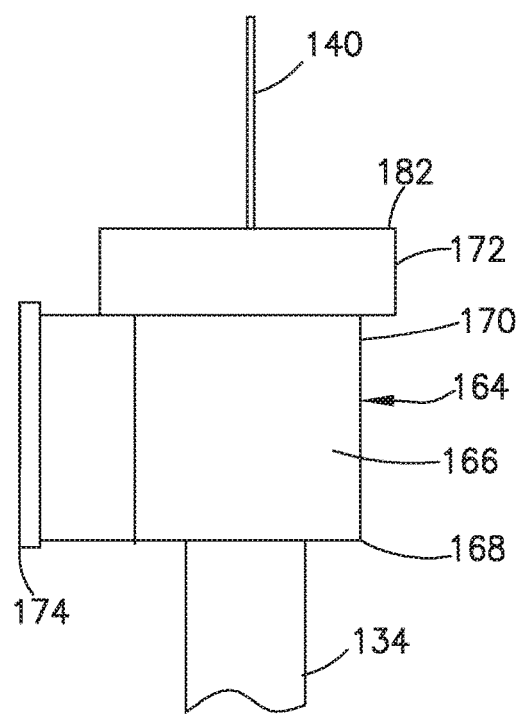
FIG. 18 is a side view of the shield member in the retracted position.
Figure 19:
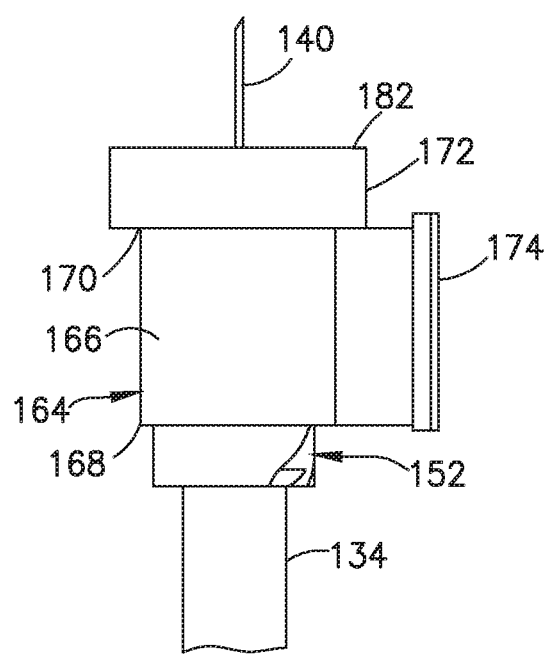
FIG. 19 is a side view with the shield member in the extended position.
Figure 20:
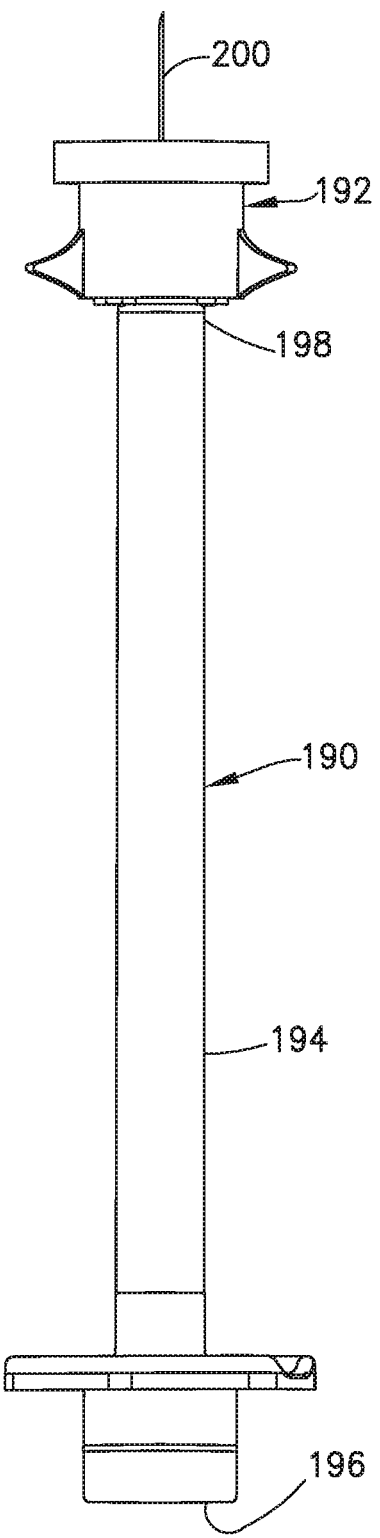
FIG. 20 is a side view of the syringe assembly in another embodiment.
Figure 21:
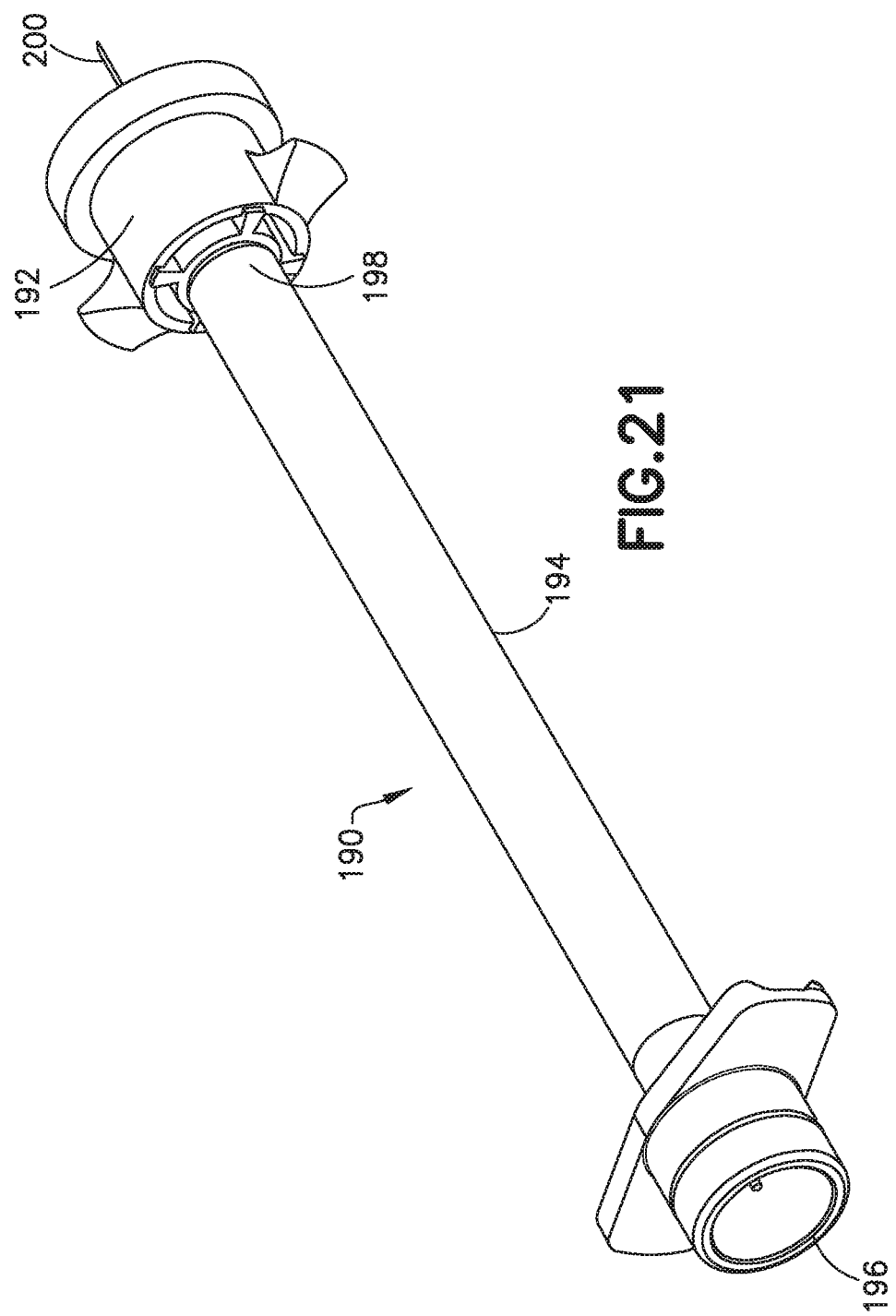
FIG. 21 is a perspective view of the syringe assembly of FIG. 20.

The detent 176 projects inwardly from the inner surface 178 of the body 166. In the embodiment shown, the detent 176 is oriented at the proximal end 168 and is configured for sliding within the guide groove 152. During use of the syringe assembly, the shield 164 is initially oriented in the retracted position shown FIG. 13 and FIG. 18 where the detent 176 is received in the proximal end of the inclined section 154 of the guide groove 152. The shield 164 in the position shown in FIG. 18 provides an exposed portion of the needle 140 having an effective length for piercing the septum of a drug reservoir for filling the syringe. After filling the syringe, the shield 164 is manually moved to the extended position shown in FIG. 19. The detent 176 slides within the inclined section 154 so that the shield rotates about the axis of the base 142 until the detent reaches the distal end of the inclined section. The shield 164 can be rotated about the axis of the base 142 where the detent 176 slides within the transverse section 158. The detent 176 slides into the recess 160 and past the detent 176 to the end portion 180 to capture the detest and resist rotation of the shield back to the original position. The shield 164 in the extended position shown in FIG. 19 provides an exposed portion of the needle 140 having a length less than the exposed length needle and the shield is in the retracted position. The syringe assembly can then be used to inject the patient where the needle 140 penetrates the skin of the patient to a depth corresponding substantially to the exposed length of the needle shown in FIG. 19. The distal end face 182 of the collar 172 contacts the skin of the patient to limit the depth of penetration of the needle.

In the embodiment show, the guide groove is formed on the adapter and the detent is formed on the shield. Alternatively, the part can be reversed so that the guide groove is formed on the shield and the detent is formed on the adapter.

Referring to FIGS. 20-27, another embodiment of the syringe assembly 190 having a shield 192 is shown. The syringe assembly 190 is similar to the previous embodiments and includes a syringe barrel 194 having an open proximal end 196 for receiving a plunger and a distal end 198. The needle 200 is coupled to the distal end of the syringe barrel and extends axially from the distal end.

Figure 22:
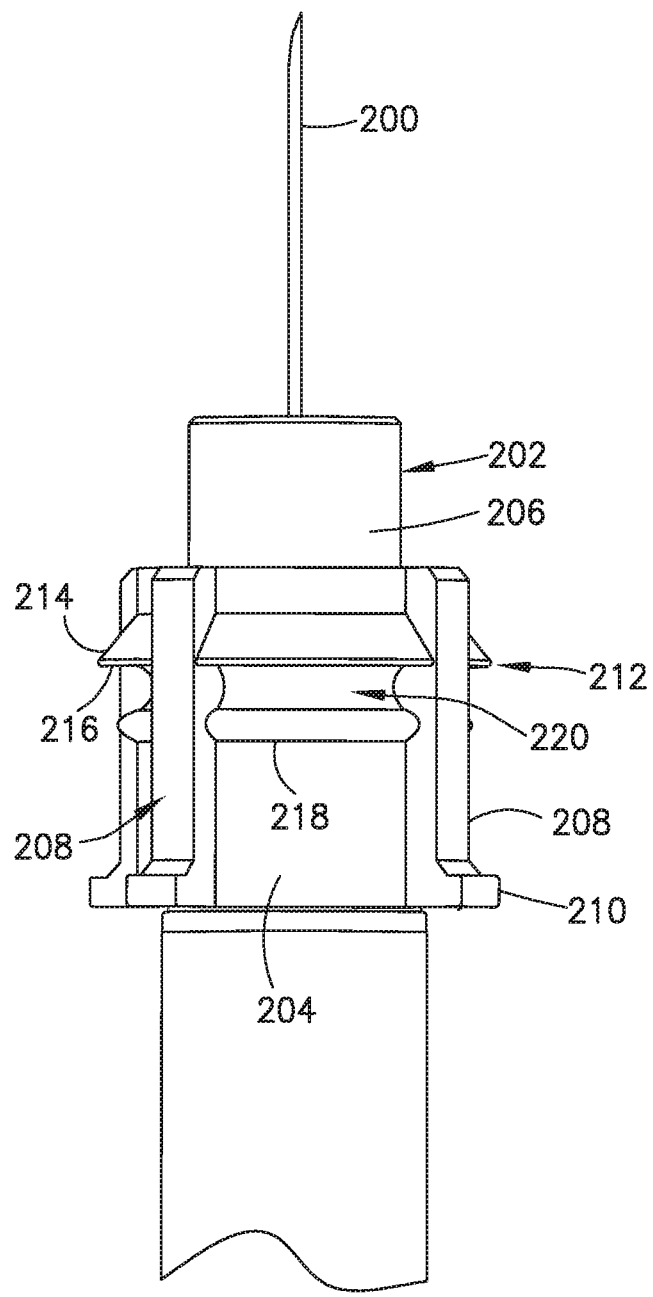
FIG. 22 is a side view of the syringe and adapter of FIG. 20 showing the connecting mechanism without the shield member.
Figure 24:
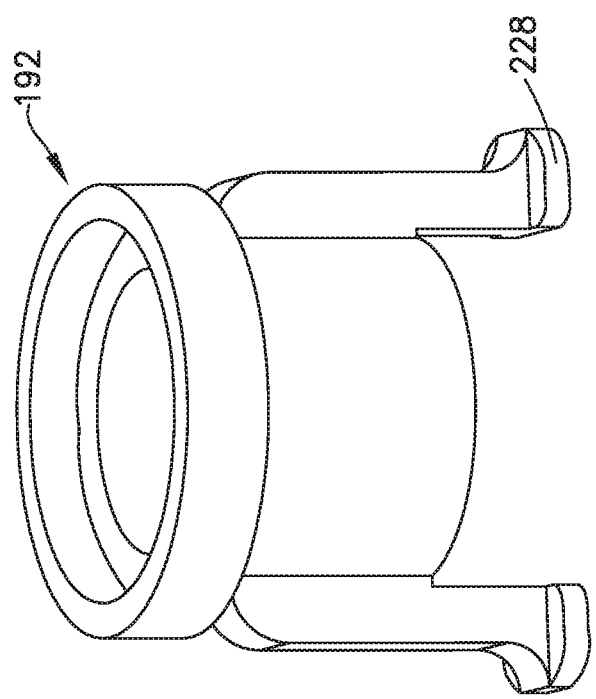
FIG. 24 is a perspective view of the shield member of an alternative embodiment of FIG. 20.

In the embodiment shown an adapter 202 is coupled to the distal end of the syringe barrel 194. In alternative embodiments, the adapter can be integrally formed with the syringe barrel. The adapter 202 has a substantially cylindrical base 204 and a cylindrical tip 206 extending from the distal end of the base 204. The needle 200 extends from the tip 206 as shown in FIG. 22.

The base 204 has longitudinally extending guide ribs 208 that extend between the proximal end and distal end of the base 204. The proximal end of the guide ribs 208 have a lip 210 projecting radially outward forming a stop member for the sliding movement of the shield 192. An annular flange 212 is provided at the distal end of the base 204 and extends around the circumference of the base. In the embodiment shown, the flange 212 has an incline distal face 214 and a substantially flat proximal face 216 forming a surface extending in a radial direction substantially perpendicular to the longitudinal axis of the base and the syringe assembly. An annular rib 218 is spaced from the flange 212 to form an annular recess 220 the embodiment shown. The rib 218 has a radial dimension less than the radial dimension of the flange 212.

Figure 23:
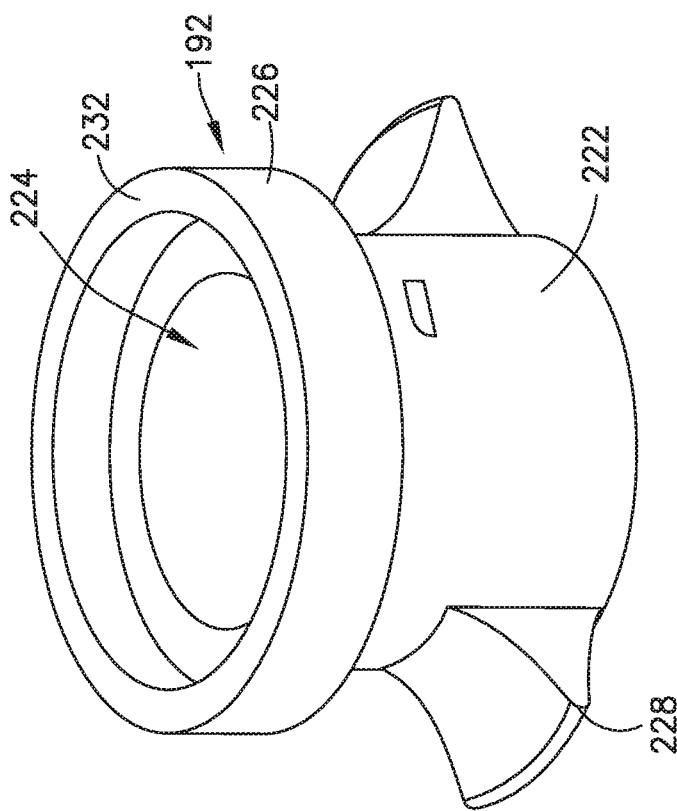
FIG. 23 is a perspective view of the shield member in an embodiment of the syringe assembly of FIG. 20.

The shield 192 has a cylindrical shaped body 222 formed by a cylindrical side wall and having an axial open passage 224. The axial passage 224 has a dimension corresponding substantially to the outer surface of the guide ribs 208 for enabling the shield 192 to slide axially on the guide ribs 208 and the adapter 202. The distal end of the body 222 has an annular collar 226 extending distally from the body 222. The collar 226 has a diameter greater than the diameter of the body 222 as shown in FIG. 23. The outer surface of the body 222 is provided with projections 228 to assist the user and manipulating the shield relative to the adapter. In the embodiment shown in FIG. 23, two projections are spaced on opposite sides of the body 222. In the embodiment shown in FIG. 24, the projections 228 extends in an axial direction and have a dimension sufficient to enable the user to manipulate the shield.

Figure 25:
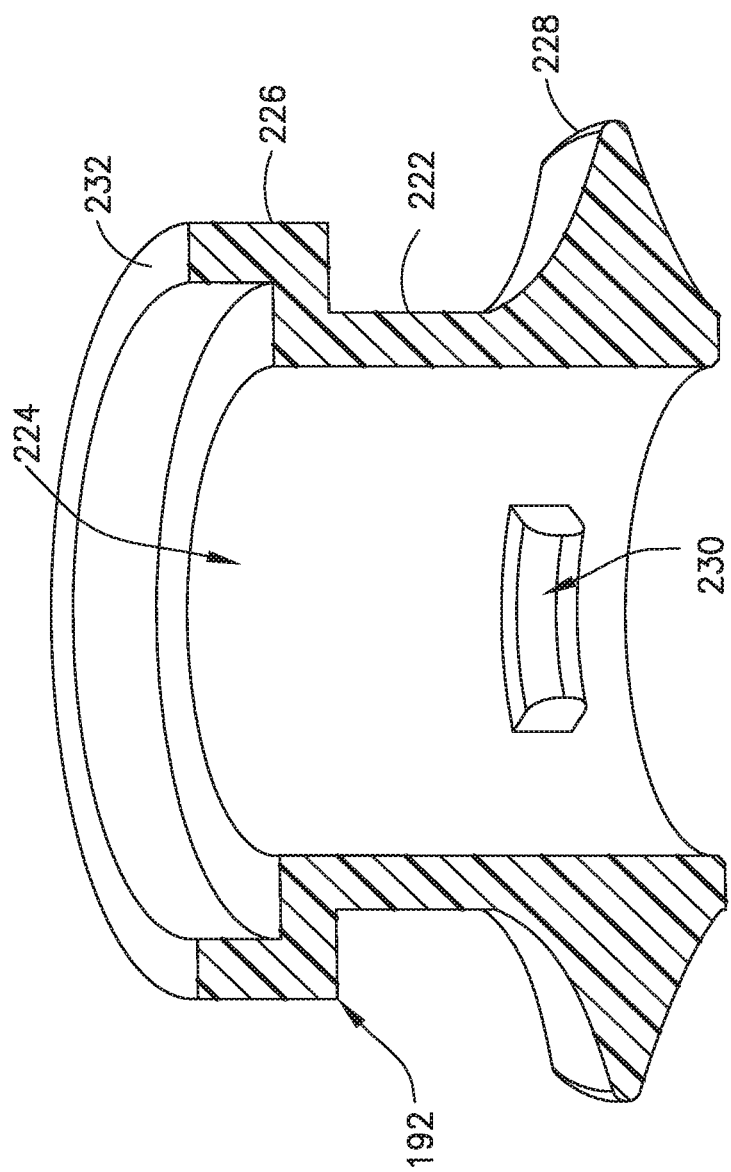
FIG. 25 is a cross sectional view of the shield member of FIG. 23.
Figure 26:
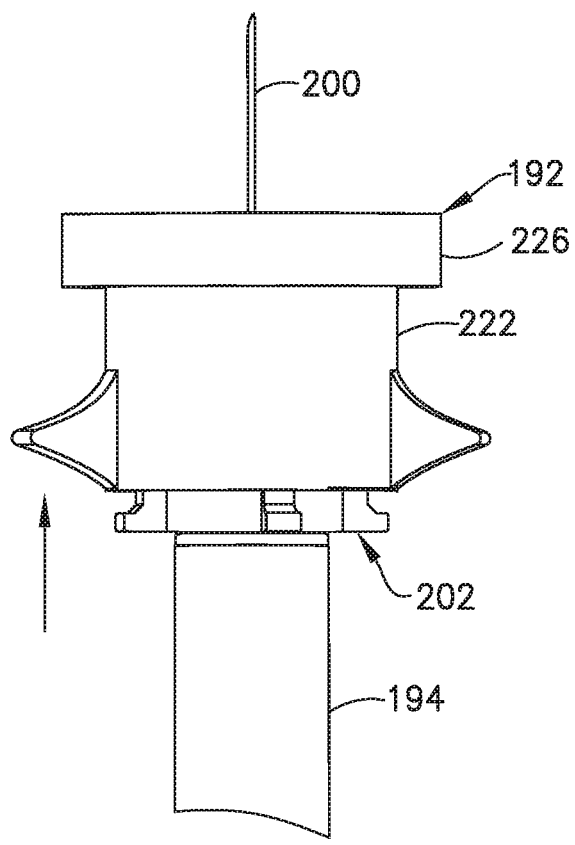
FIG. 26 is a side view showing the shield member in a retracted position.
Figure 27:
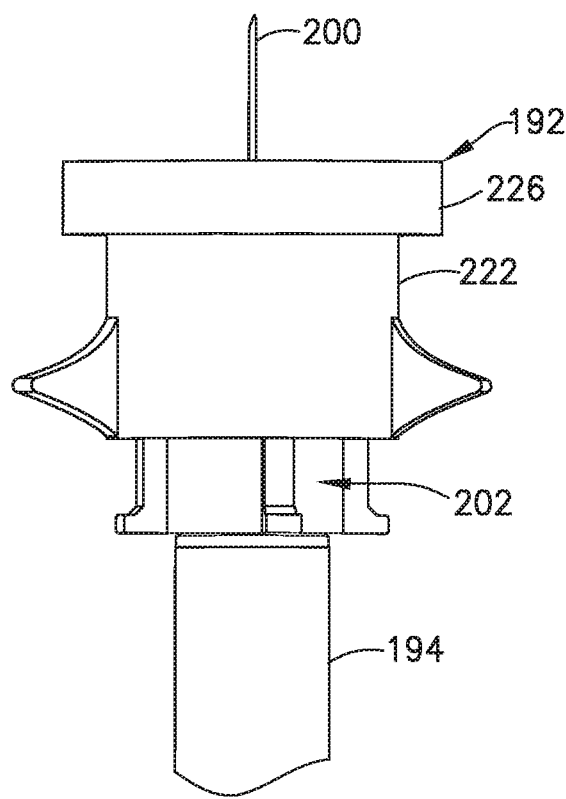
FIG. 27 is a side view showing the shield member in an extended position.

Referring to FIG. 25, the inner surface of the body 222 includes at least one inwardly extending detent 230. The detent 230 is formed at the proximal end of the body 222 and has a radial dimension to slide axially between adjacent guide ribs 208. The detent 230 has an axial dimension sufficient to fit within the annular recess 220. The shield 192 slides over the distal end of the adapter so that the detent 230 slides over the inclined face 214 of the flange 212. The shield 192 is initially positioned in the retracted position shown in FIG. 26 where the proximal end of the body 222 contacts the lips 210 of the guide ribs 208. In the position shown in FIG. 26, the needle 200 has an exposed length to enable the syringe to be easily filled by piercing the septum of a reservoir. The shield 192 is then moved manually by sliding axially toward the distal end of the adapter 202 to the position shown in FIG. 27 where the detent 230 slides over the rib 218 and snaps into the annular recess 220. In the position shown in FIG. 27, the distal face 232 of the collar 226 forms and an exposed length of the needle having a length less than the length when the shield is in the retracted position of FIG. 26. The rib to 18 and the annular recess 220 have a dimension sufficient to retain the detent 230 with sufficient force to resist sliding movement of the shield to the retracted position during penetration of the needle into the patient. The needle penetrates the skin of the patient to a depth where the distal face 232 of the collar 226 contacts the surface of the skin to limit the depth of penetration.

Figure 28:
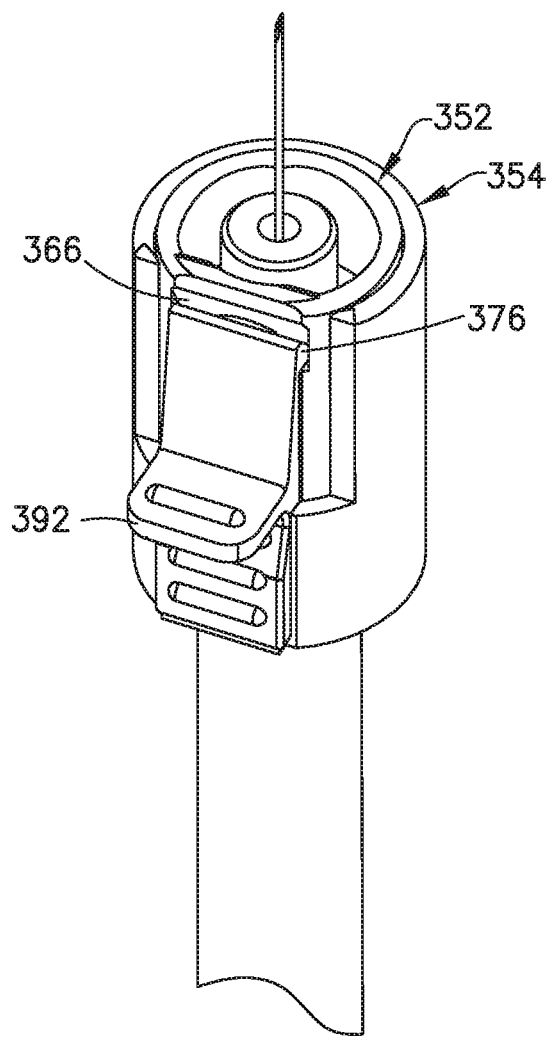
FIG. 28 is a perspective view of the shield and adapter in another embodiment.
Figure 29:
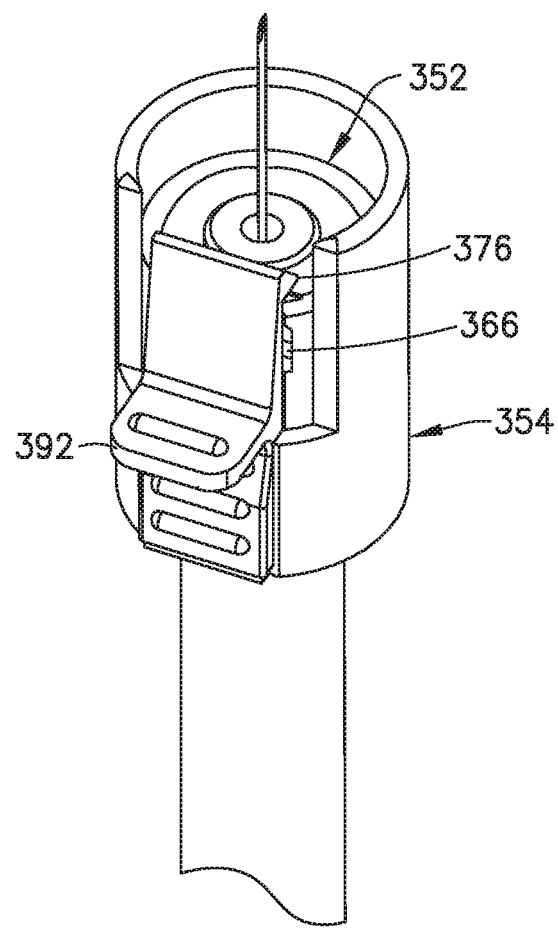
FIG. 29 is a perspective view of the embodiment of FIG. 28 showing the shield in the extended position.
Figure 30:
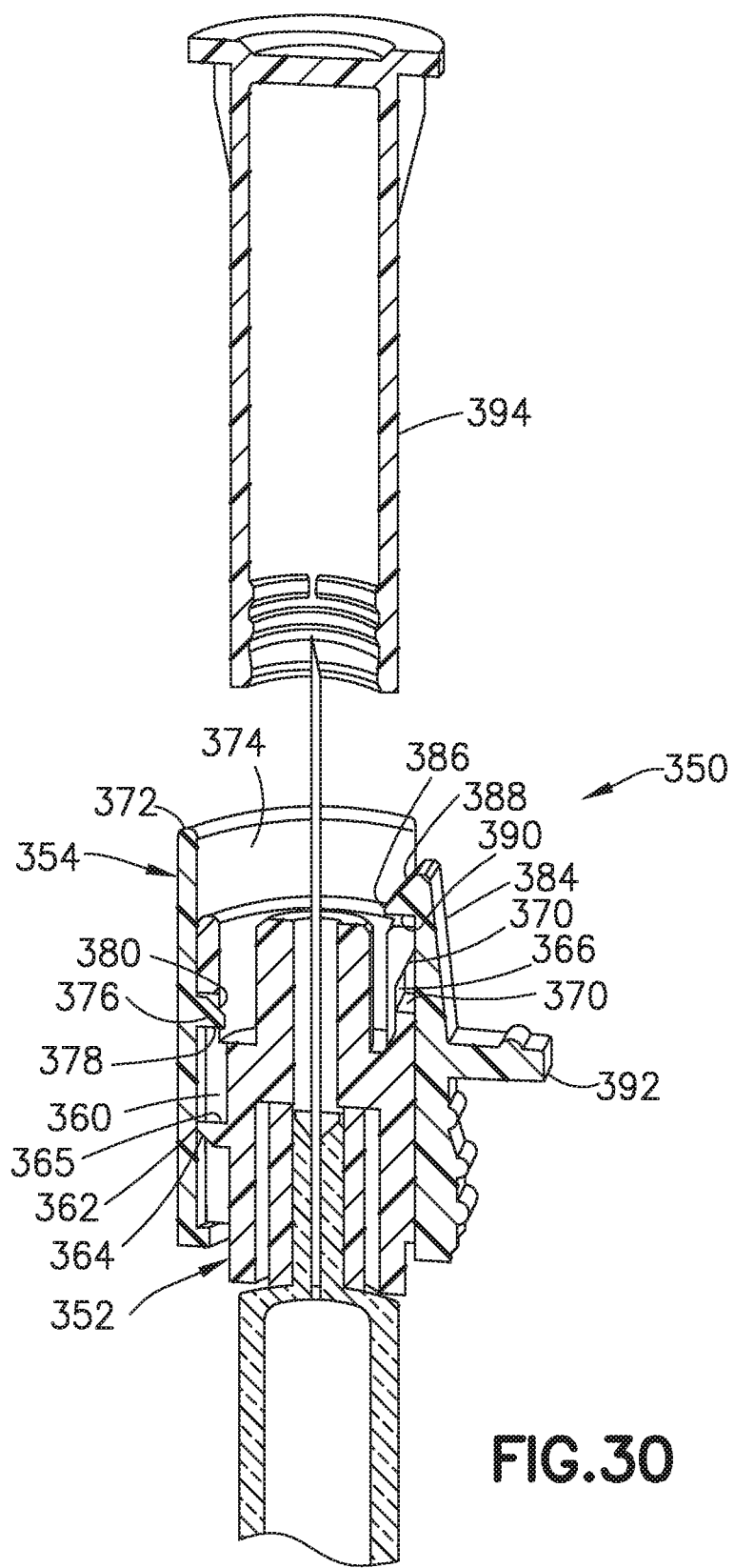
FIG. 30 is cross sectional view of the adapter of FIG. 28.

Referring to FIGS. 28 to 30, another embodiment of the movable shield and adapter assembly 350 is shown. The adapter 352 is coupled to the syringe barrel as in the previous embodiments and the shield 354 slides on the adapter between a retracted position and an extended position. The adapter 352 includes an open proximal end forming an internal passage 356 having ribs or other mechanism for coupling the adapter 352 to the distal end of the syringe barrel. The body has a longitudinally extending slot 360 with a detent 362. The detent 362 has an inclined surface 364 facing the proximal end toward the syringe barrel, and a flat surface 365 extending perpendicular to the center axis and facing the distal end of the body. On a side opposite the slot 360 and detent 362 is a recess 366 on an outer surface. The recess 366 has flat surface 368 extending perpendicular to the center axis and an inclined surface 370.

The shield 354 has a substantially cylindrical body 372 with a central passage 374 having a dimension corresponding to the dimension of the adapter 352. A detent 376 projects inwardly from the side wall of the body 372 for sliding longitudinally in the slot 360 and engaging the detent 362 in the slot. The detent 376 has a flat surface 378 extending perpendicular to the center axis and facing a proximal end, and an inclined surface 380 facing toward the distal end. The detent 376 slides in the slot 360 with the sliding movement of the shield 354 on the adapter 352. The detent 376 forms a stop member to engage the detent 362 to limit sliding in the proximal direction. The slot 360 has an end wall at the distal end of the slot to limit the sliding movement of the shield in the distal direction.

The shield 354 has a flexible tab 384 cantilevered to the body of shield for engaging the recess 366 in the adapter 352. The flexible tab 384 is hinged to the body of the shield and can bend outward relative to the body. The distal end of the tab 384 has an inwardly extending detent 386 that engages a flat side surface of the adapter. The detent 386 has an inclined distal face 388 and a flat face 390 extending perpendicular to the longitudinal axis. The detent 386 is received in the recess in the adapter when the shield is in the retracted position. The shield 354 is pushed in the distal direction by a thumb tab 392 where the detent 386 slides from the recess and hooks onto the end of the adapter as shown in FIG. 29 to cover a portion of the needle and the detent 376 engages the end wall of the slot 360. The flexible tab 384 can be flexed outwardly to release the detent 386 from the end of the adapter 352 to slide the shield 354 to the retracted position of FIG. 28 to expose the needle for filling and aspirating. A cover 394 shown in FIG. 30 can be attached to the end of the adapter 352 to cover the exposed end of the needle until ready for use.

The foregoing embodiments and advantages are exemplary and are not intended to be construed as limiting the scope of the invention. The description of alternative embodiments are intended to be illustrative, and not to limit the scope of the present invention. Various modifications, alternatives, and variations will be apparent to those skilled in the art, and are intended to fall within the scope of the invention. The features of different embodiments and claims may be combined with each other as long as they do not contradict each other. Accordingly, all such modifications are intended to be included within the scope of this invention as defined in the appended claims and their equivalents.

The invention claimed is:
1. A syringe assembly comprising:
a syringe barrel having a proximal end and a distal end, and a needle extending from said distal end of said syringe barrel; and
a shield member positioned on a body coupled to said syringe barrel for moving between a first position where said needle is exposed a first length and a second position covering a portion of said needle where a second length of said needle is exposed that is less than said first length, and said shield member has a retaining mechanism configured for retaining said shield in said second position, and said shield member is movable by rotation or sliding in a transverse direction relative to said body when the shield member is in the second position to retain said needle shield in said second position exposing the second length of the needle.

2. The syringe assembly of claim 1, wherein said shield member has side wall and a bottom wall with an opening for moving axially on said body.

3. The syringe assembly of claim 2, wherein said body has a side face complementing a dimension and shape of said opening in said bottom wall, and where said body has a recess at a distal end receiving said bottom wall of said shield member whereby said shield member is rotatable relative to said body when said shield member is in said second position.

4. The syringe assembly of claim 3, wherein said body includes a post at a distal end of said body, said post having an outer face complementing an inner edge of said opening in said shield member.

5. The syringe assembly of claim 4, wherein said post has an annular rib extending radially outward for capturing said bottom wall of said shield member between said annular rib and a distal face of said body, and where said post has a dimension to enable said shield member to rotate when said shield is in said second position.

6. The syringe assembly according to claim 1, wherein said body has a detent extending outwardly, and said shield member has a recess receiving said detent, said recess having a configuration to enable said shield member to move in an axial direction relative to said body to said second position and to move in a transverse direction when said shield member is in said second position.

7. The syringe assembly according to claim 6, wherein said recess has a first section extending in an axial direction relative to said syringe, and a second section extending in a transverse direction relative to said first section to slide said shield member in said transverse direction.

8. The syringe assembly according to claim 7, wherein said shield member has an opening receiving said needle, said opening having a dimension to enable said shield member to slide to said second position.

9. The syringe assembly according to claim 7, wherein said first section of said recess is oriented at an incline relative to an axial direction of said body.

10. A syringe assembly comprising:
a syringe barrel having a proximal end and distal end, and a needle extending from said distal end of said syringe barrel; and
a movable shield member coupled to said distal end of said syringe barrel and configured for sliding in an axial direction with respect to said syringe barrel between a first position to expose a first portion of said needle having a first length, and a second position to cover the proximal end of the needle to expose a second portion of said needle having a second length less than said first length, and where said shield member is movable when in the second position by rotation or by sliding in a transverse direction relative to the axial direction to a retaining position to retain said shield member in the second position.

11. The syringe assembly according to claim 10, wherein said shield member has an axial opening to receive said needle, and where said opening has an inner dimension whereby said shield member can move in said transverse direction relative to said needle.

12. The syringe assembly according to claim 11, wherein said syringe barrel has a detent received in a recess having a configuration to enable said shield member to move in said axial direction and in said transverse direction.

13. The syringe assembly of claim 12, wherein said opening has first section extending in an axial direction for moving said shield member in said axial direction, and a second section for moving said shield member in said transverse direction.

14. The syringe assembly of claim 10, wherein said shield member has a side wall and a bottom wall with an opening for receiving a base coupled to said syringe, said base having a configuration for enabling movement of said shield member, and enabling rotation of said shield member to the retaining position when said shield member is in said second position.

15. The syringe assembly of claim 14, wherein said base has an axial face and a post with an annular rib extending radially outward and spaced from said axial face of said base forming a recess for receiving said bottom wall of said shield member when said shield member rotates to the retaining position.

16. The syringe assembly of claim 15, wherein said opening in said bottom wall of said shield member has a flat surface and where said post has a flat surface complementing said flat surface of said opening to provide a tactile sensation when said shield member is rotated with respect to said post.

17. The syringe assembly of claim 16, wherein said annular rib has a radial dimension greater than a width of said opening in said bottom wall.

18. A syringe assembly comprising:
a syringe barrel having a proximal end and distal end, a body coupled to said distal end of said syringe barrel, and a needle coupled to said distal end of said syringe barrel and extending through said body, said body having an outer surface with an annular recess; and
a movable shield member coupled to said body and configured for sliding in an axial direction with respect to said syringe barrel between a first position to expose a first portion of said needle having a first length, and a second position to cover the distal end of the syringe barrel to expose a second portion of said needle having a second length less than said first length, and where said shield member has a detent complementing said annular recess to retain said shield member in the second position.

19. A method for filling a syringe, comprising providing a syringe barrel having a proximal end and distal end, a needle coupled to said distal end of said syringe barrel, a body coupled to said distal end of said syringe barrel, and a shield member adapted for moving on said body between a first position to expose a first portion of said needle having a first length, and a second position to expose a second portion of said needle having second length less than said first length;
moving said shield member to the first position to expose the needle and filling said syringe;
moving the shield member to the second position to expose the second portion of the needle; and
maintaining the shield member in the second position by moving said shield member in a second rotational or transverse direction relative to the axis of said syringe.

* * * * *